United States Patent
Sarachan et al.

(10) Patent No.: US 9,607,375 B2
(45) Date of Patent: Mar. 28, 2017

(54) BIOLOGICAL DATA ANNOTATION AND VISUALIZATION

(71) Applicant: GENERAL ELECTRIC COMPANY, Schenectady, NY (US)

(72) Inventors: Brion Daryl Sarachan, Schenectady, NY (US); John Frederick Graf, Ballston Lake, NY (US); Anup Sood, Clifton Park, NY (US); Vidya Pundalik Kamath, Greenville, SC (US)

(73) Assignee: Eileen B. Gallagher, Niskayuna, NY (US)

( * ) Notice: Subject to any disclaimer, the term of this patent is extended or adjusted under 35 U.S.C. 154(b) by 106 days.

(21) Appl. No.: 14/729,982

(22) Filed: Jun. 3, 2015

(65) Prior Publication Data

US 2016/0358326 A1 Dec. 8, 2016

(51) Int. Cl.
*G06K 9/00* (2006.01)
*G06T 7/00* (2017.01)
*G06F 19/00* (2011.01)
*G06F 17/30* (2006.01)

(52) U.S. Cl.
CPC ...... *G06T 7/0012* (2013.01); *G06F 17/30259* (2013.01); *G06F 19/321* (2013.01); *G06T 2207/30024* (2013.01)

(58) Field of Classification Search
CPC ......... G06T 7/0012; G06T 2007/30024; G06F 19/321; G06F 17/30259

USPC .................................................. 382/128, 133
See application file for complete search history.

(56) References Cited

U.S. PATENT DOCUMENTS

| | | | | |
|---|---|---|---|---|
| 8,168,568 | B1* | 5/2012 | Mehta | G01N 33/5041 |
| | | | | 435/6.19 |
| 2009/0124542 | A1* | 5/2009 | Hageman | C12Q 1/6883 |
| | | | | 514/1.1 |
| 2012/0288879 | A1* | 11/2012 | Altiok | G01N 33/5011 |
| | | | | 435/7.92 |
| 2013/0123328 | A1* | 5/2013 | Yu | A61K 31/436 |
| | | | | 514/44 A |
| 2013/0189274 | A1* | 7/2013 | Berkenblit | C12Q 1/6886 |
| | | | | 424/145.1 |
| 2014/0222443 | A1* | 8/2014 | Danenberg | G01N 33/57407 |
| | | | | 705/2 |
| 2015/0064210 | A1* | 3/2015 | GuhaThakurta | G01N 33/564 |
| | | | | 424/192.1 |

* cited by examiner

*Primary Examiner* — Tom Y Lu
(74) *Attorney, Agent, or Firm* — Eileen B. Gallagher

(57) ABSTRACT

Dynamic linking of pathway maps and cell maps is disclosed in certain embodiments. In such embodiments, the pathway maps are linked to spatially-localized regional nucleic acid data (e.g., sequence data), as opposed to non-spatially selected nucleic acid data. The pathway map and cell map data may be linked so that interactions results in changes or updates to the linked map, such as the selection or highlighting of cells exhibiting pathway map characteristics specified by a user of updating of node values or states to correspond to that of a cell or cells selected by the user.

22 Claims, 16 Drawing Sheets

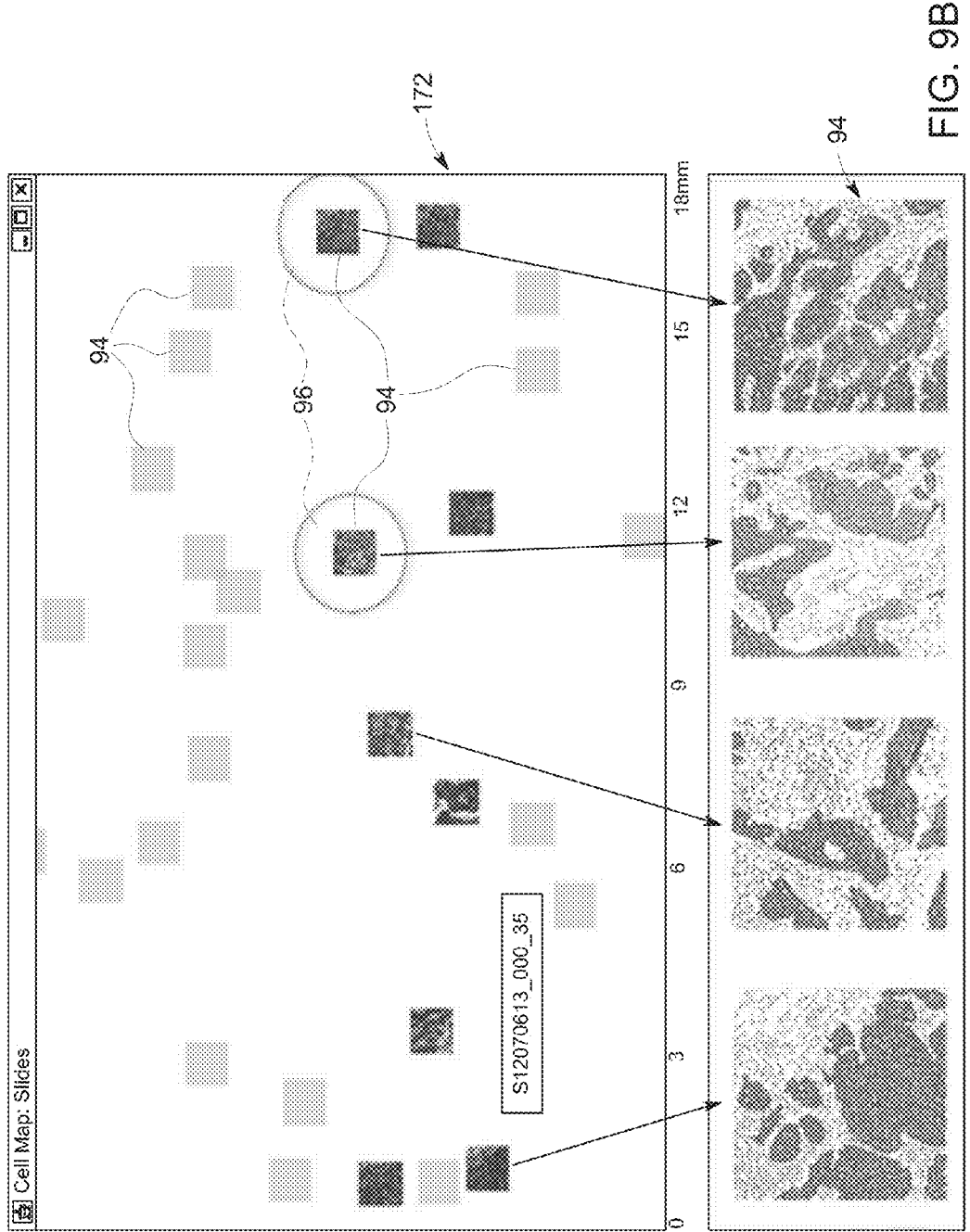

BIOLOGICAL DATA ANNOTATION AND VISUALIZATION

BACKGROUND

The subject matter disclosed herein relates to the association and analysis of biological and biochemical data acquired from a variety of sources.

The proliferation of biological and biochemical tools has led to substantial increases in the amount of information available about biological and biochemical systems, though it may be difficult to associate the myriad types and sources of information together in a meaningful manner. As a result, information may be available that is difficult to parse in isolation but which is also difficult to easily associate with related information that would yield insight when analyzed in combination.

It is now possible to acquire expression data for both proteins and nucleic acid sequences for both patients and populations, as well as sequence data for both proteins and nucleic acid sites. In addition, cellular level data and images can be acquired. However, each of these different types of information are typically acquired using different types of processes and/or systems, and thus may not be readily combinable or associated. Thus, despite the extent of this information that can be obtained and existing knowledge of the associated regulatory pathways, it may still be difficult to fully exploit the extent of the information that may be available.

By way of example, even with a full array of conventional data acquisition and analysis tool, deciphering deregulated pathways and biological states in complex diseases in an individual or a population may remain challenging. For instance, there are over 20,000 protein-encoding genes in the human genome. Most signaling and metabolic pathways involve 100's if not 1,000's of essential genes, RNA and protein molecules in specific molecular states (e.g. phosphorylation, binding) and cellular compartments (nucleus, cytosol, plasma membrane). The large number of molecule types, their concentrations in different cells and sub-cellular compartments, and the dynamics of biological processes are just some of the challenges faced in associating and analyzing available biological and biochemical data.

BRIEF DESCRIPTION

In one embodiment, a computer-based method is provided for interactively evaluating image and data for a tissue sample. In accordance with this method, a pathway map is displayed comprising a plurality of nodes linked to nucleic acid sequence data for one or more spatially localized regions-of-interest within a tissue sample. A cell map is displayed depicting a set of cells present within a field-of-view of the tissue sample. The cell map is linked to a plurality of biomarker expression data displayed for the tissue sample. One or more inputs are received specifying values or states for one or more nodes of the pathway map. Based on the one or more inputs, cells within the cell map that exhibit biomarker expression corresponding to the values or states specified for the one or more nodes are highlighted.

In a further embodiment, a computer-based method is provided for interactively evaluating image and data for a tissue sample. In accordance with this method, a pathway map is displayed comprising a plurality of nodes linked to nucleic acid sequence data for one or more spatially localized regions-of-interest within a tissue sample. A cell map is displayed depicting a set of cells present within a field-of-view of the tissue sample. The cell map is linked to a plurality of biomarker expression data for the tissue sample. One or more inputs are received selecting one or more cells of the cell map. Based on the one or more inputs, values or states of one or more nodes within the pathway map are set to correspond to the nucleic acid characteristics of the one or more selected cells.

In an additional embodiment, a processor-based system is provided. The processor-based system includes one or both of a memory or storage device storing one or more executable routines for the analysis of region-specific nucleic acid sequence data and cellular or sub-cellular biomarker expression data and one or more processors configured to execute the one or more executable routines. The one or more routines, when executed, cause acts to be performed comprising: displaying a pathway map comprising a plurality of nodes linked to nucleic acid sequence data for one or more spatially localized regions-of-interest within a tissue sample; displaying a cell map depicting a set of cells present within a field-of-view of the tissue sample, wherein the cell map is linked to a plurality of biomarker expression data for the tissue sample; receiving inputs setting one or more node values or states within the pathway map or selecting one or more cells within the cell map; if the inputs set one or more node values or states within the pathway map, highlighting cells within the cell map that exhibit biomarker expression corresponding to the values or states specified for the one or more nodes; or if the inputs select one or more cells within the cell map, setting values of one or more nodes within the pathway map to correspond to the nucleic acid characteristics of the one or more selected cells.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 9A and 9B collectively show a sample screen depicting associated cell image and pathway map data in conjunction with a calculated slide view and select regions of interest, in accordance with further aspects of the present disclosure;

DETAILED DESCRIPTION

Figure 1:
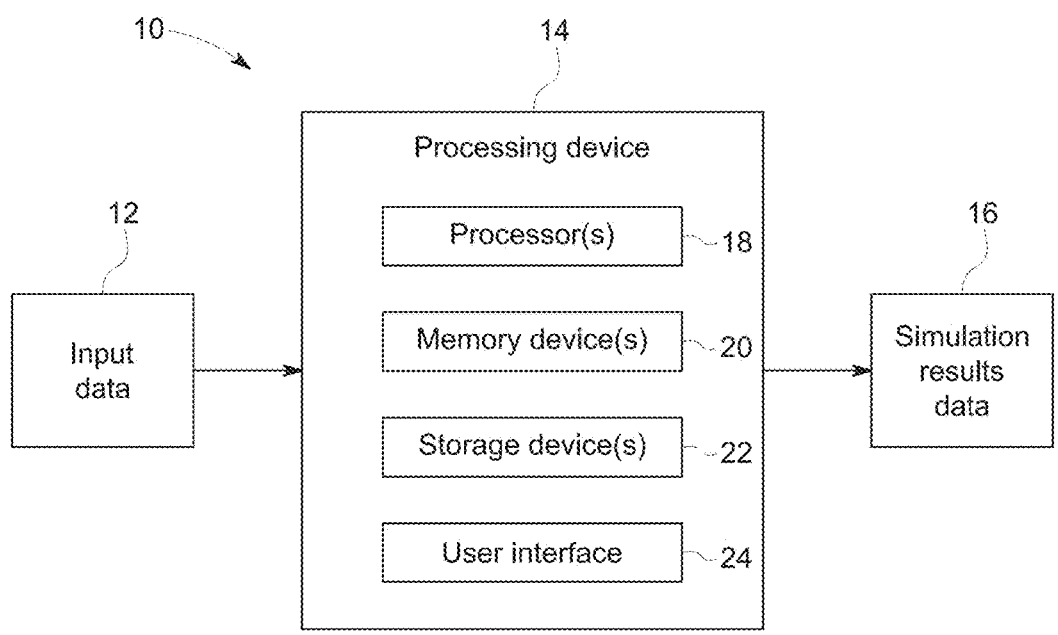
FIG. 1 is a block diagram of an embodiment of a processor-based system for integrating, displaying, and querying data, in accordance with aspects of the present disclosure.

The present discussion relates to associating and analyzing biological and biochemical data (including expression, sequence, and image data) from disparate sources to facilitate analysis and understanding. By way of example, certain approaches discussed herein may be useful in interpreting multiplexed immunofluorescence (IF) and fluorescent in situ hybridization (FISH) tissue image measurements in a context of pathways and biological processes. Such analyses may have previously been challenging given the limited number of probe measures relative to the large number of pathways and system network states. Integration of IF and FISH tissue measures with other types of data (including, but not limited to: genomics, transcriptomics, proteomics, and metabolomics, and so forth) has also been difficult using conventional approaches. Yet increasingly such combined or associated measures from a subject may be desirable when trying to decipher deregulated pathways and biological states in complex diseases. With this in mind, the present approach provides useful tools (e.g., software tools) that facilitate data integration, analysis, and visualization in a pathway context.

To provide some context for certain of the data acquisition approaches discussed herein and for the amount and type of data involved, Multiomyx technology (available from General Electric Company) provides the capability to measure IF protein concentrations for up to 60 proteins within the same cell. Fluorescent in situ hybridization (FISH) probes provide measurements of RNA and DNA molecules at the cellular level. Having protein and RNA measurements on a per cell basis using such techniques is an improvement over traditional grind-and-find approaches, such as flow cytometry, where data at the cellular level may be lost. Instead, the traditional approach is to obtain measures of each protein and RNA concentration, and DNA sequence averaged over a large number (e.g., millions) of cells. This capability, as discussed herein, to resolve measures of protein, DNA, and RNA expression and/or sequence at the single cell level while also preserving spatial information provides for powerful pathway analysis approaches.

In one example, multiplexed IF tissue imaging measures are integrated with other types of data including, but not limited to, DNA sequencing, RNA expression, and DNA-FISH measures. In one such embodiment, these different types of data can be overlaid onto (or otherwise integrated into) biochemical pathway maps and the associated data used to perform one or both of gene set enrichment analysis and pathway scoring analysis. From within the combined data, features may be interactively selected and/or manipulated from among the high content data, with resulting impacts or selections shown in the pathway views. Furthermore, in certain implementations, a researcher can select a specific pathway state and then query cells that exhibit the selected state to view how the cells are spatially distributed in the tissue.

The present discussion, therefore, provides for the use of tools in the analysis, modeling, simulation, and/or representation of biological data drawn from disparate sources. As discussed herein, the present tools may be embodied and implemented as executable applications running on a programmed general-purpose or application-specific processor-based platform. Prior to describing in detail the operation of such applications, an example of a suitable processor-based system 10 is briefly discussed with reference to FIG. 1. In particular, FIG. 1 is a block diagram of an embodiment of a processor-based system 10 for integrating, annotating, visualizing, and querying biological and/or biochemical data drawn from various sources, as discussed herein.

Input data 12 may be directly input by one or more users, may be acquired from an imaging or sequencing system at a local or remote location, may be acquired from a database of patient records, researcher or physician notes, clinical studies, or online research tools, or may be acquired from other local or network accessible resources. The input data 12 may be provided to the processing device 14 in a variety of standard and/or non-standard data formats (e.g., image files, binary files, text files, spreadsheets, databases, etc.), and the data may include varying levels of detail, common or differing nomenclature, and/or common or different color, coordinate, or reference systems. The input data 12, as discussed herein, is provided to a processing device 14, which is used to execute one or more operations on the input data 12 in accordance with present embodiments, such as to integrate, visualize, and/or query the data 12 in a raw or processed form.

The processing device 14 includes one or more processors 18, memory devices 20, and storage devices 22. The processor(s) 18 may be used to execute routines as discussed herein for processing the data 12. Moreover, the processor(s) 18 may include one or more microprocessors, such as one or more "general-purpose" microprocessors, one or more special-purpose microprocessors and/or application specific integrated circuits (ASICS).

The memory device(s) 20 may include a volatile memory, such as random access memory (RAM), and/or a nonvolatile memory, such as read-only memory (ROM). The memory device(s) 20 may store a variety of information and may be used for various purposes. For example, the memory device(s) 20 may store processor-executable instructions (e.g., firmware or software) for the processor(s) 18 to execute, such as instructions for implementing the present approaches.

The storage device(s) 22 (e.g., nonvolatile storage) may include ROM, flash memory, a hard drive, or any other suitable optical, magnetic, or solid-state storage media. The storage device(s) 22 may store data (e.g., input data 12, processing results, etc.), instructions (e.g., software or firmware for processing data 12, etc.), and so forth.

The depicted processing device 14 includes a user interface 24. The user interface 24 enables an operator to input parameters associated with the input data 12 or with the processing of the data 12. The user interface 24 also enables an operator to select options or to configure processing of the data 12. As may be appreciated, the user interface 24 may include a keyboard, a mouse, or any suitable device for inputting data, making selections, and/or operating the processing device 14. Furthermore, the user interface 24 may include a display to present data, such as the simulation results data 16. The user interface 24 may also include a printer for printing data, such as for printing simulation results data 16.

With the preceding hardware discussion in mind, approaches discussed herein provide for the design and use of tools to integrate, analyze, and view high content tissue data in a pathway context and/or in a tissue view. For example, in certain embodiments, such a tool may integrate immunofluorescence (IF) (including multiplexed IF and/or other biomarker expression data) and fluorescent in situ hybridization (FISH) tissue imaging measures with other types of data including, but not limited to, microarray, DNA sequencing and expression measures, and RNA sequencing and expression measures. In certain implementations, such a tool may overlay or integrate different types of such data onto pathway or regulatory maps. In such approaches, the tool may be used to perform one or both of gene set enrichment analysis or pathway scoring analysis. Further, the tools, as discussed herein, may be used to interactively select features from the high content data and to show how the selected features, or changes to these features, impact the pathway view. In addition, in certain embodiments a researcher can use such a tool to select a specific pathway state and to query cells that exhibit the state for additional details regarding these cells and/or to view how the cells that exhibit the selected state are spatially distributed in the tissue. By way of example, IF, FISH, DNA sequence, and/or RNA sequence data may be obtained for or integrated with tissue images, including for different selected regions of interest of the tissue images. From such views, a user may view variants, copy number, RNA and protein measures, and so forth (such as for selected regions of interest on the tissue images) on associated pathway maps. Conversely, on the associated pathway map, selected pathway states or conditions may be identified and corresponding regions highlighted or shown on the tissue images, such as down to the cellular or subcellular level. In this manner, a user may be able to interactively differentiate between tissues or cells and within tissue samples across multiple pathway map nodes.

Figure 2:
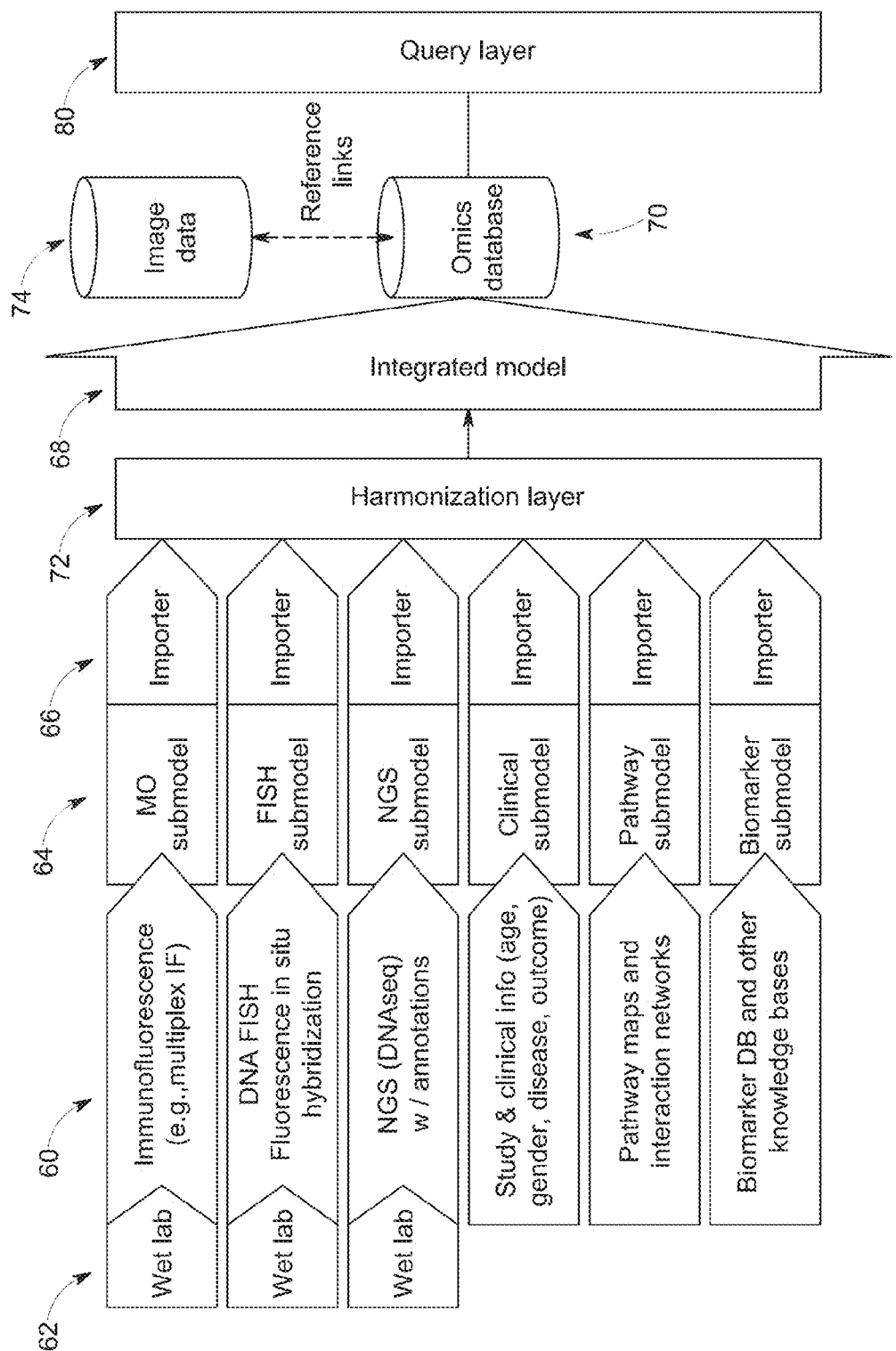
FIG. 2 is a high-level depiction of the aggregation of different data sources and types for use in a query tool, in accordance with aspects of the present disclosure.

With these concepts in mind, and turning to FIG. 2, a high-level view of the relationship between various data sources and the present tool is provided. In this example, various pipelines 60 corresponding to different data sources and types (e.g., DNA sequencing, imaging (IF and FISH), pathway, biomarker expression, and so forth) are shown. Certain of the pipelines 60 (e.g., IF, FISH, and nucleic acid sequencing) originate in wet lab settings 62 (i.e., as the result of clinical or medical lab work for a patient or cohort of patients). Conversely, other pipelines may originate from online research community or data store sources, from records of clinical studies, from databases or catalogs of biomarker activity and/or pathway maps, and so forth. Patient, clinical and study data may include demographic data (e.g., gender, age, height, weight, and so forth) as well as other clinical values, such as diagnoses, symptoms, and so forth. The various pipelines 60 in these examples may access data of various types and formats, such as flat files or data stored in databases (e.g., relational databases).

With respect to the various types of wet lab data, it is worth noting that there may not be strict correspondence between the shape and/or size of sample regions for different techniques. For example, turning briefly to FIG. 3, an example of a slide 90 on which a tissue sample 92 is affixed is shown. Such a slide 90 and tissue sample 92 may be suitable for generating multiplexed IF images, such as a series of images, each stained with one or more different IF biomarker probes such that each image depicts biomarker expression levels for the respective biomarker(s) selected for that round of imaging. When viewing such images, a user may specify several respective fields-of-view 94 corresponding to a representative portion (e.g., spatial distribution) of the sample 92 and the desired objective strength for the microscope in question.

In addition, one or more sequencing sections or regions 96 may also be taken from the sample 92. For example, such sequencing regions 96 may be extracted or lifted after multiplexed IF imaging and one or both of DNA or RNA sequence and expression levels determined within the region 96. In this manner, sequencing data may be obtained for different spatially localized sections of the sample 92 so that some degree of spatial information is retained with respect to the sequence data. As with the fields-of-view 94, the sequencing regions 96 may be selected to be representative of and spatially distributed with respect to the sample 92.

Figure 3:
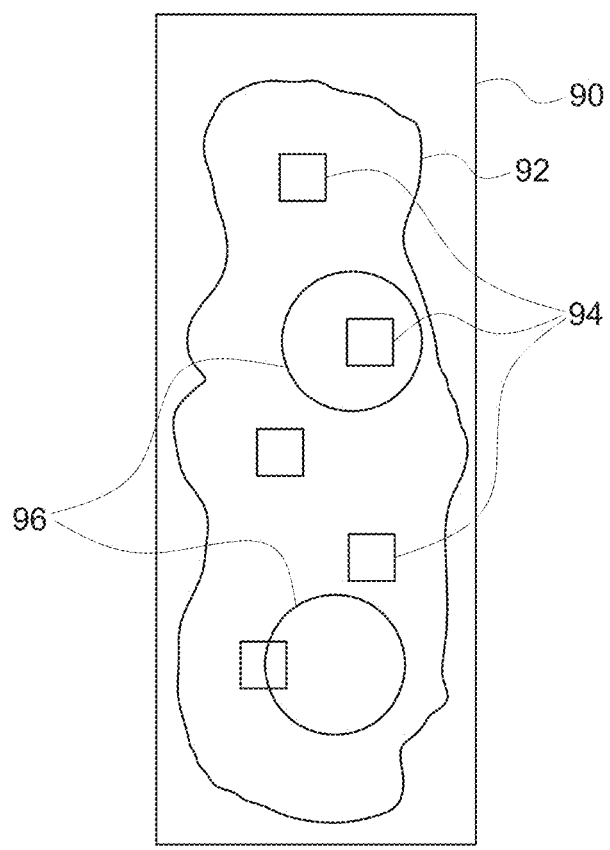
FIG. 3 depicts a tissue sample suitable for imaging and acquiring cellular samples, in accordance with aspects of the present disclosure.

Though not necessarily to scale, as depicted in FIG. 3, the sequencing regions 96 and the imaging fields-of-view 94 may differ in both size, spatial location, and/or shape, with the depicted example showing the sequencing regions being larger and differently shaped than the fields-of-view 94. In the depicted example, the fields-of-view 94 are square and are approximately 0.76 mm across, while the sequencing regions circular and are approximately 2 mm in diameter. As a result, to the extent that the size, spatial location, and/or shape of the sequencing regions 96 and fields-of-view 94 differ, there may not be precise correspondence between the sequence or other nucleic acid information acquired for a given sequencing region 96 with the biomarker expression data acquired for a generally corresponding field-of-view 94. Further, while biomarker expression and other measures generated for a given field-of-view 94 may be granular to the cellular or sub-cellular level, nucleic acid data (sequence and otherwise) acquired for a given sequencing region 96 may be granular only down to the level of the sequencing region. That is, data acquired for a sequencing region 96 may be aggregated or averaged over the respective sequencing region 96, but not to a higher level of granularity (e.g., to cells or sub-cellular structures within the sequencing region 96).

However, as will be appreciated, both the size and shape of the fields-of-view and the sequencing regions 96 will be a function of the respective imaging and sampling technologies employed. Thus, in other implementations the sequencing regions 96 may be the same size or smaller than the fields-of-view 94, including down to the cellular, or even sub-cellular level to the extent that the sampling technology and sequencing technology permits. Similarly, in other implementations the sequencing regions 96 may be shaped differently than what is shown, including having geometries similar to or the same as the fields-of-view 94, or even having arbitrary shapes or distributions, such as where a user specifies the individual cells or groups of cells to be sampled for sequencing.

With this in mind, and turning back to FIG. 2, in the depicted example, the various pipelines 60 may be embodied as or incorporated into respective submodels 64. Each pipeline 60 may also have an associated importer 66 by which the submodel 64 and/or raw or processed data obtained by the respective pipeline 60 may be imported into an integrated model 68 and, ultimately, into a database 70 (e.g., an "omics" database). In the depicted example, a harmonization layer 72 may also be provided. Such a harmonization layer 72, when present, may harmonize the respective submodels 64 or datasets to account for differences in nomenclature and/or coordinate systems (in the case of image data). In addition, in the depicted example an external set of image data 74 or image database may be provided that can be referenced by or incorporated into the database 70, such as via one or more reference links.

Lastly, a query layer 80 is provided by which a user may access and interact with the database 70. By way of example, via the query layer 80, a user may formulate a complex biological query based on a question of interest. The query may in turn be processed by the query layer 80 and used to access the relevant data and/or models within the database 70. Results of the query may then be analyzed, visualized, and/or exported via the query layer 80.

Figure 4:
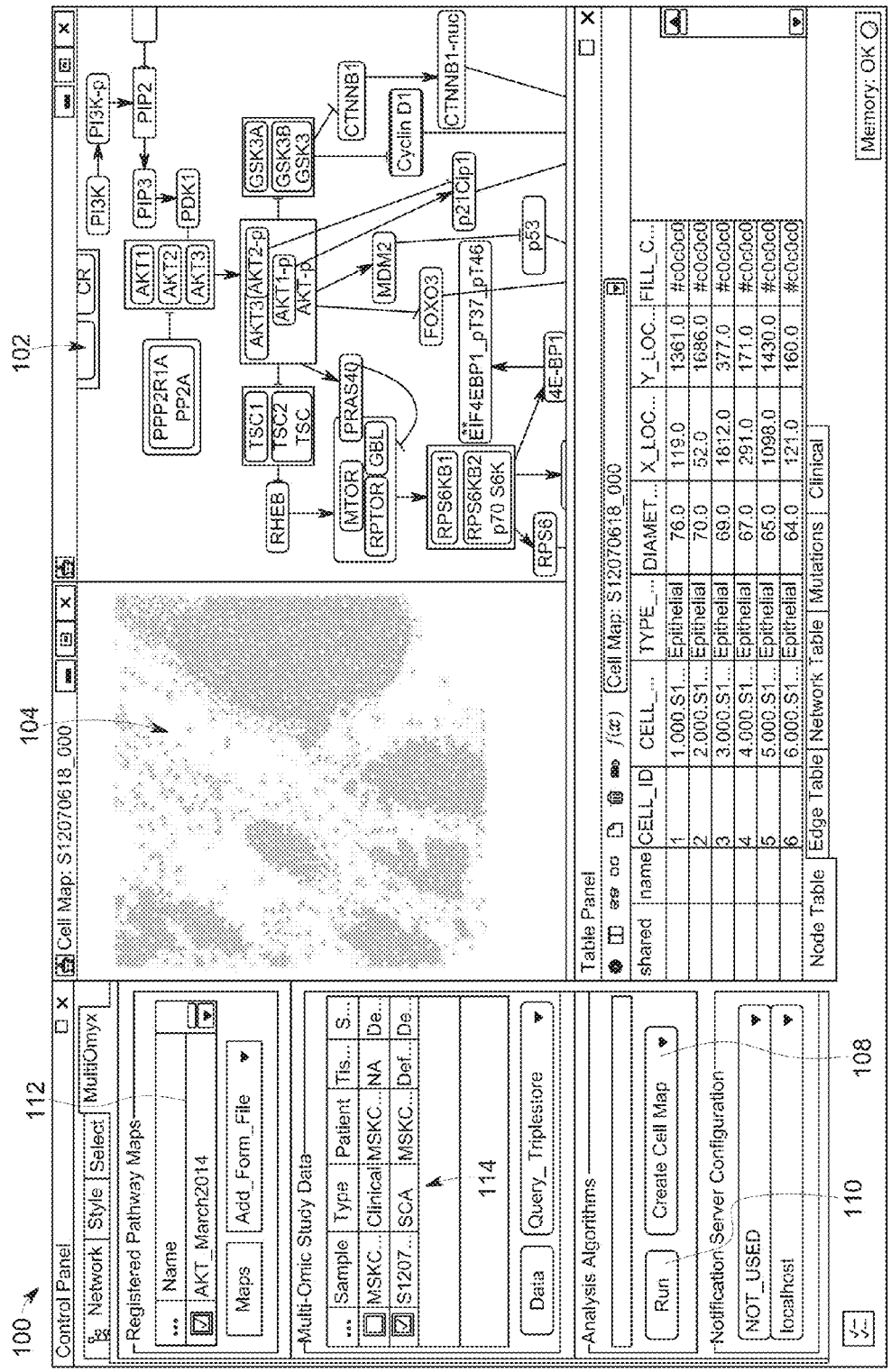
FIG. 4 shows a sample screen depicting associated cell image and pathway map data, in accordance with aspects of the present disclosure.

With the preceding discussion in mind, examples of tool implementations and uses are provided to facilitate explanation of the present concepts. For example, turning to FIG. 4, a screen 100 is displayed of an implementation of a tool in accordance with the present approach where the screen 100 provides a linked, concurrent view of cell map (e.g., tissue image) and pathway data. In certain implementations the underlying subject, (e.g., patient) tissue, and/or study data may be selected via a displayed interface 114 (e.g., a study data panel), where available subject, tissue, and/or study data may be displayed, such as in a tree format or a hierarchical list.

In the depicted example, a single pathway map 102 (e.g., a metabolic and/or signaling pathway) and a single cell map 104 are shown, though it should be appreciated that, depending on the analysis and queries of interest, more than one pathway map 102 and/or cell map 104 may be displayed at one time, such as in separate panes of the screen 100. As discussed herein, the cell map or tissue images 104 may correspond to an image of a field-of-view 94 taken from a larger tissue sample 92 and may thus display individual cell or sub-cellular structures within the tissue sample 92. The cell maps or tissue images 104 may therefore correspond to one or more standardized fields-of-view selected based on a given protocol or operation, such as to achieve a desired spatial representation, or may correspond to one or more user-selected or specified fields-of-view. The cell map 104 may be created by selection and execution of a suitable analysis algorithm, such as may be implemented using selection box 108 and execution button 110. For example, in the depicted screen the analysis algorithm "Create Cell Map" has been selected at box 108 and executed to create cell map 104 representing a selected field-of-view 94. In certain embodiments, the interface may provide options (such as via a popup menu) allowing a user to configure the cell map 104, such as to add or clear a region of interest from the view, to select cells within the cell map 104 based on one or more of biomarker, cell type, DNA and/or RNA sequence or expression, user applied highlighting, and so forth.

The pathway map 102 may be obtained and loaded from a variety of online or proprietary data sources and may be loaded from local files or imported from external data sources. In the depicted example, a pathway map 102 may be added, such as via a control interface 112, from a selectable list and registered via the interface. Once added, the pathway map 102 may be displayed graphically as a network of nodes and edges. In certain embodiments, the interface may provide options (such as via a popup menu) allowing a user to configure the pathway map, such as to add or clear a pathway map from the view or to set a state for a node or link within the pathway map 102, such as to set the state of a pathway node to average, high, low, or undefined. By way of example, in one implementation a user may set a state of a selected node based on a three-state model, e.g., <x is low, x-to-y is medium, and >y is high. In view of the various selection and configuration options provided to the user, cells may be highlighted in the cell map 104 based on a pathway map state specified by the user, such as by specifying a state for one or more nodes of the pathway map 102. Conversely, the state of one or more nodes of the pathway map 102 may be set based upon the user selection of one or more cells within the cell map 104. That is, the linkage between the cell map 104 and pathway map 102 allows a user to make changes or selection in either map that results in changes made to the state or display of the other map.

In certain implementations, the pathway maps 102 undergo an automated pathway map registration process, which maps the pathway nodes and edges to standard accession numbers (e.g., NCBI) of proteins, RNA, and genes. Performing such a registration process on the pathway nodes may facilitate algorithm implemented analysis across disparate data types, as discussed herein.

With respect to the pathway map(s) 102, in certain implementations one or more visual indicators (e.g., colors and/or symbols) may be displayed in conjunction with the nodes of the pathway map 102. As used herein, a node 120 of a pathway map 102 should be understood to convey a variety of possible information. For example, in certain implementations a respective node 120 can represent or convey a specific molecule, a specific molecular state of such a molecule (e.g., whether the molecule is phosphorylated, bound, and so forth), and/or a spatial location (e.g., extracellular or sub-cellular compartment locations (such as the nucleus, cytosol, plasma membrane, and so forth)). As used herein, and as discussed in greater detail below, a node 120 can link to protein IF measures (such as may be conveyed in the tissue images or maps) specific to the same relative spatial locations.

Figure 5:
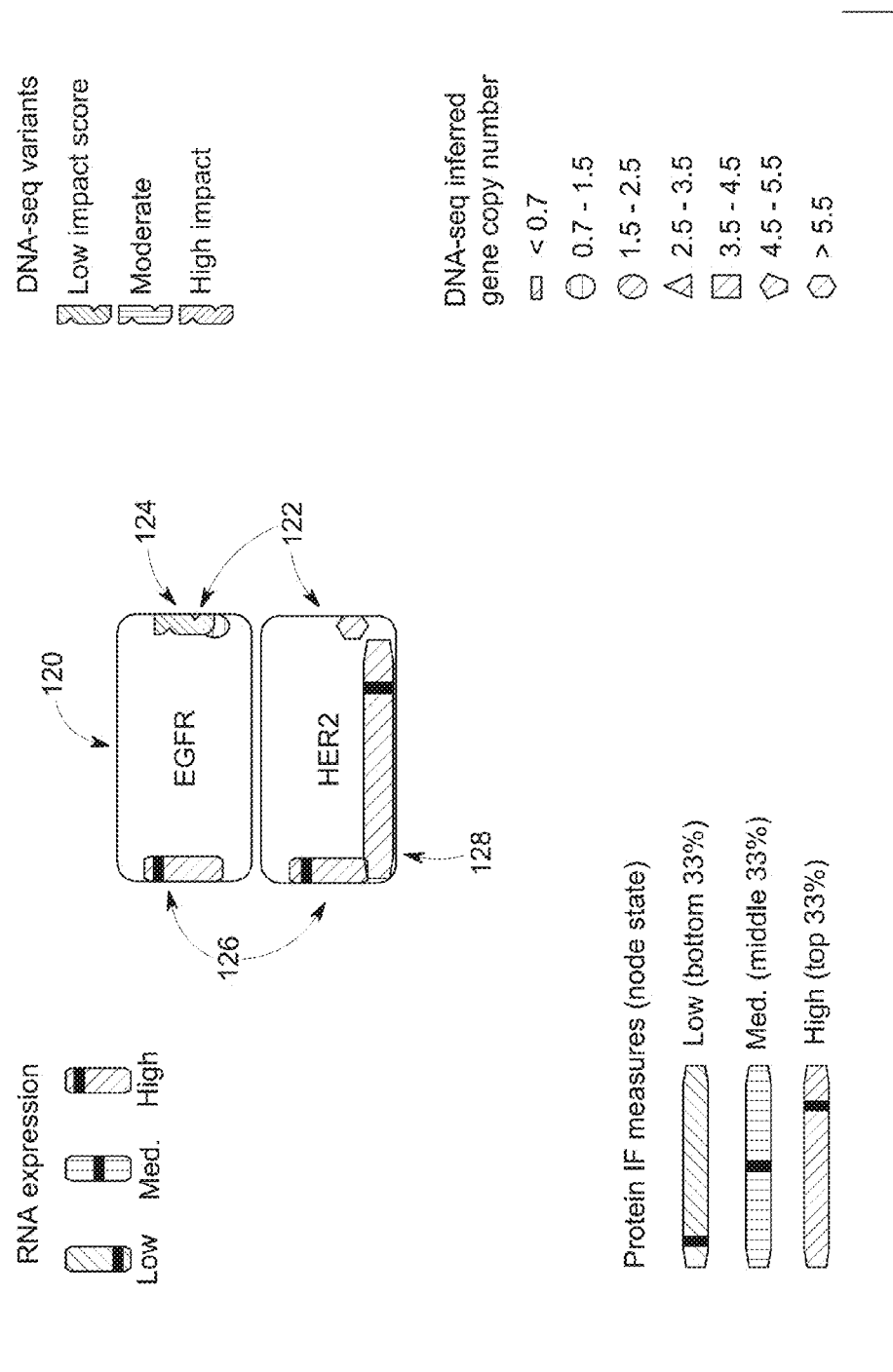
FIG. 5 depicts an example of visual annotation that may be associated with a pathway node to convey subject specific measurement data, in accordance with aspects of the present disclosure.

With respect to the use of visual indicators with the nodes 120, and turning to FIG. 5, two sample nodes 120 (e.g., EGFR and HER2) which may be part of a pathway map 102 are depicted with various examples of indicators that may be used to convey or to specify information about a node 120 in an implementation. By way of example, the displayed or indicated information may correspond to biomarker expression (e.g., derived for cells or sub-cellular structures, individually or in aggregate, within a given field-of-view 94) and/or nucleic acid (e.g., RNA, DNA, and so forth) sequence data (e.g., derived for a given sequencing region 96) for a subject for which a tissue cell map is concurrently displayed. In the depicted example, indicators are shown which convey an inferred gene copy number (indicator 122 and accompanying legend), DNA sequencing variant impact (indicator 124 and accompanying legend), RNA expression measures (indicator 126 and accompanying legend), and multiplexed immunofluorescence protein measures (for HER2) (indicator 128 and accompanying legend).

In the depicted example, the subject has an inferred HER2 gene copy number of 5.6 from the DNA sequencing data so a red hexagon indicator 122 is displayed in the lower right hand corner of the HER2 node. The HER2 RNA expression is high indicated by a red vertical bar indicator 126. The HER2 protein IF measure is also high represented by the horizontal red bar indicator 128. The EGFR gene has DNA mutations as indicated by the appearance of the DNA strand symbol indicator 124 on the right side of the EGFR node. The probability that these mutations are pathogenic has been scored as low (e.g., displayed as a blue DNA strand symbol indicator). The impact of DNA mutations may be computed from a multivariate logistic model that generates a value representing the probability of a DNA mutation being pathogenic vs. nonpathogenic or using other suitable models. In certain implementations, the details of a node's DNA mutations may be invoked for display, such as viewed in a table, by selecting a given node.

Figure 6:
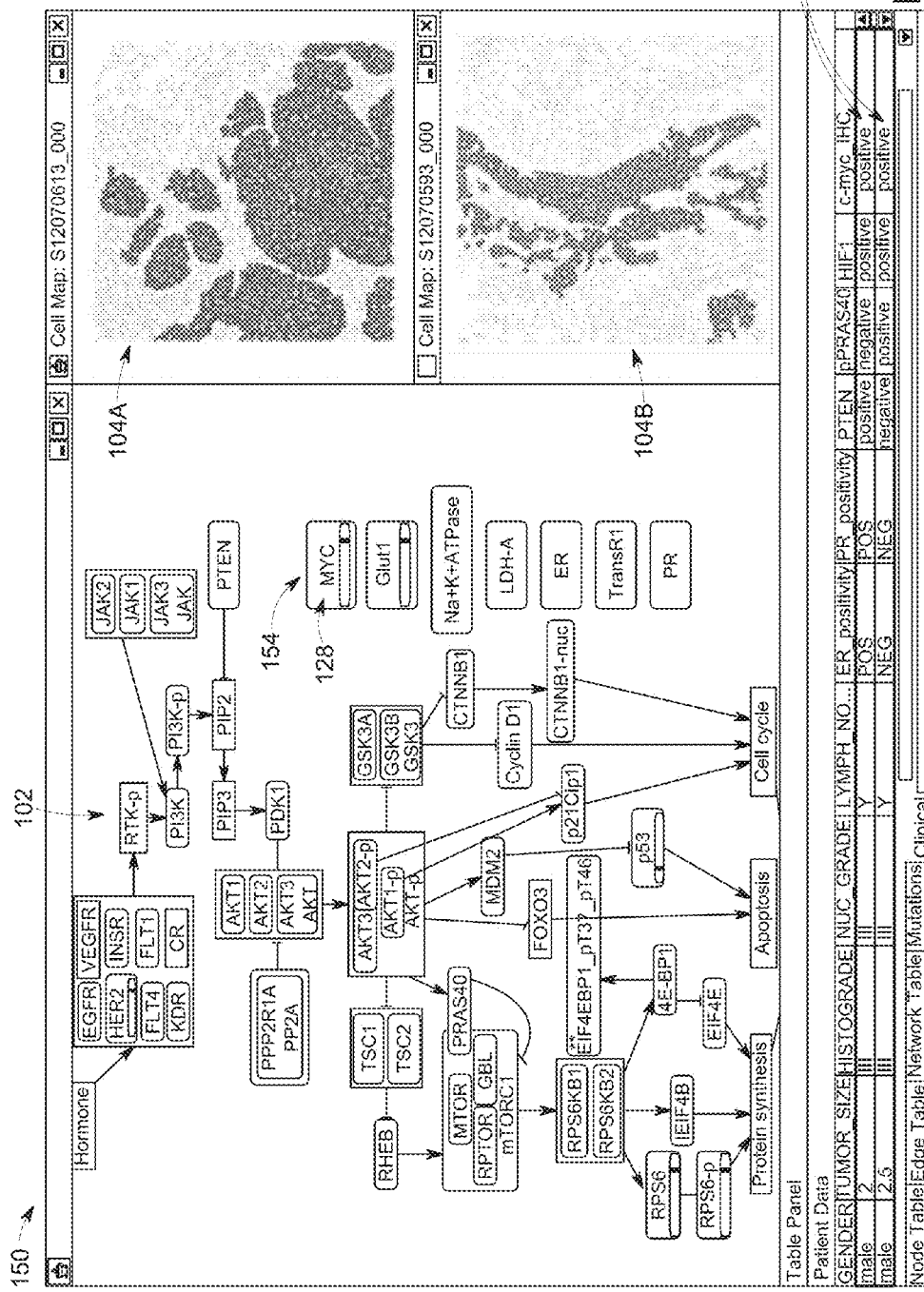
FIG. 6 shows a sample screen depicting associated cell image and pathway map data, in accordance with further aspects of the present disclosure.

With the preceding discussion in mind, various examples are provided of the use of a data integration and query tool in accordance with the present approach. For example, turning to FIG. 6 a sample screen 150 is depicted of an implementation where a user has set or otherwise specified the state of one or more pathway nodes 120 in the pathway map 102 resulting in cells that exhibit the specified pathway state at the nodes 120 in question being highlighted (e.g., highlighted red) in the cell maps 104. Further, in the depicted example, cell maps 104A and 104B corresponding, respectively, to two different subjects are displayed concurrent with the pathway map 102, allowing the reviewer to compare the different subjects based on the specified criteria.

To further elaborate on the depicted example, the samples in question are both MYY IHC-positive, as indicated in selected patient data fields 152. Correspondingly, the pathway map 102 state has been set to for high MYC, shown by a colored or highlighted horizontal bar (e.g., indicator 128) for the MYC node 154. Further, the pathway map nodes 120 for GLUT1, HER2, RPS6 have been set to high and the pathway map node 120 for TP53 has been set to low, as shown by their respective indicator bars. In this manner, the state of the pathway 102 has been defined based on the settings of these nodes. Once the state of the pathway 102 is defined, an algorithm (e.g., Pathway>Cells) may be executed and, as an output of such an algorithm, cells in the tissue images (e.g., cells maps 104) may be highlighted which meet the defined pathway state criteria (e.g., where the measured values at the cells in question have values that meet the criteria defined by the nodes for which values have been set by the user). Thus, a user may, based on known pathways and on measured, subject specific expression and sequence data, highlight individual cells (or sub-cellular structures) within a tissue image that exhibit characteristics specified in a linked pathway map.

Figure 7:
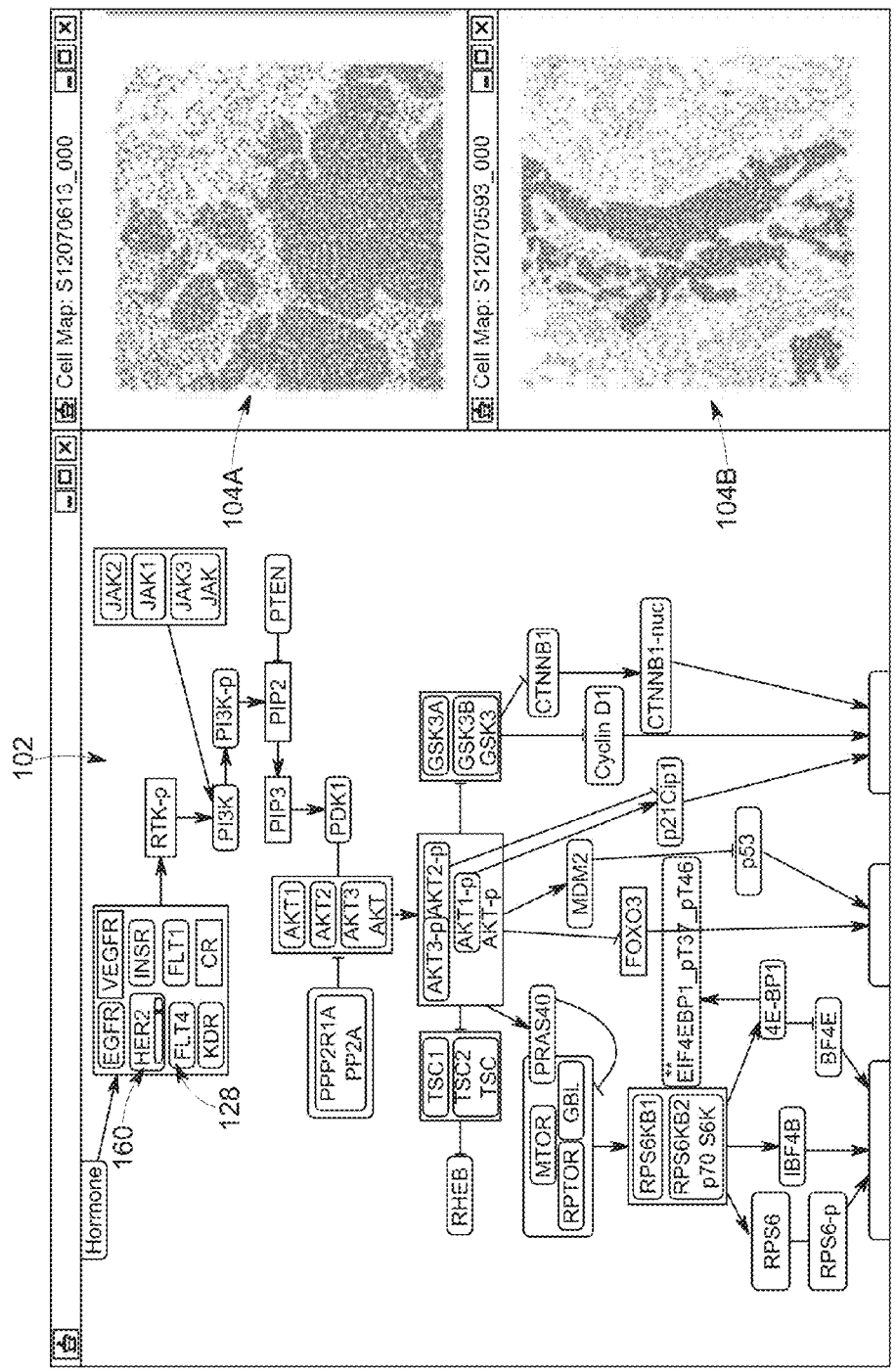
FIG. 7 shows a sample screen depicting associated cell image and pathway map data, in accordance with additional aspects of the present disclosure.
Figure 8:
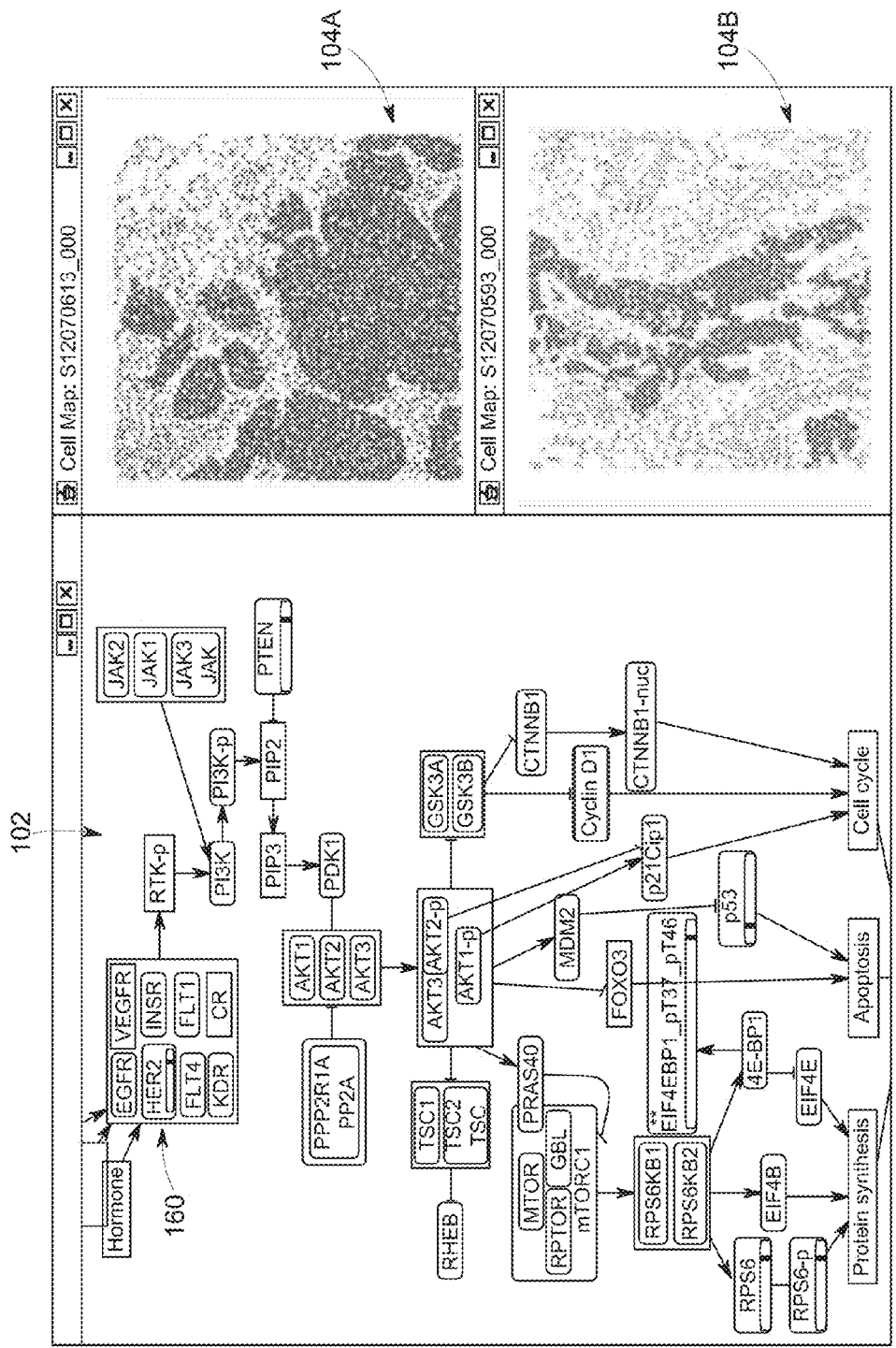
FIG. 8 shows a sample screen depicting associated cell image and pathway map data, in accordance with further aspects of the present disclosure.

Turning to FIGS. 7-9, these figures depict a more complex example involving the use of the present tool. In this example, a specific sub-population of cells is identified that exhibit a pathway state in a cancer sample from one individual and the identified pathway state is then used to screen (e.g., highlight) cells in a tissue sample from another individual. In this example, it can also be seen that cells may be highlighted in fields of view 94 located at different tissue locations.

Turning to FIG. 7, in this example cell maps 104 for two different subjects (shown as 104A and 104B) are displayed concurrent with a linked pathway map 102. All cells in cell maps 104 having high HER2 protein expression are identified in two patients by setting the HER2 node 160 in the pathway map 102 to high, shown by a colored horizontal bar (e.g., indicator 128). In this example, cells within the cell maps 104 having high HER2 are highlighted (e.g., shown in red or another specified color).

Turning to FIG. 8, from among the highlighted cells, a reviewer may select a cell or set of cells, e.g., a set of highlighted cells from one of the cell maps 104. In this example, the reviewer has selected the cells in the bottom cell map 104B that were highlighted as having high HER2 expression levels. In one implementation, the selected cells may in turn be highlighted a different color (e.g., yellow) to indicate their selected status. In this example, in response to the selection of the cells in the cell map 104B, the pathway map 102 is updated to set the state of one or more nodes 120 based on the selected cells. For example, nodes where biomarker expression and/or nucleic acid expression or sequence measures are noteworthy or aberrant may be automatically set based on the measures observed in the selected cells, as shown by indicators 122, 124, 126, 128. In this example, selected cells from one cell map are used to update the pathway map 102, which in turn causes the highlighting of the cells within the other cell map 104 (i.e., the upper cell map 104A, in this example corresponding to a tissue sample from another patient or at a different field of view within the same sample) to be updated based on the new node settings. In this manner, cells in a different patient, tissue sample, or field of view may be queried and selected by selecting cells in a given cell map (or tissue sample), which sets the state of an intermediary pathway map.

Figure 9A:
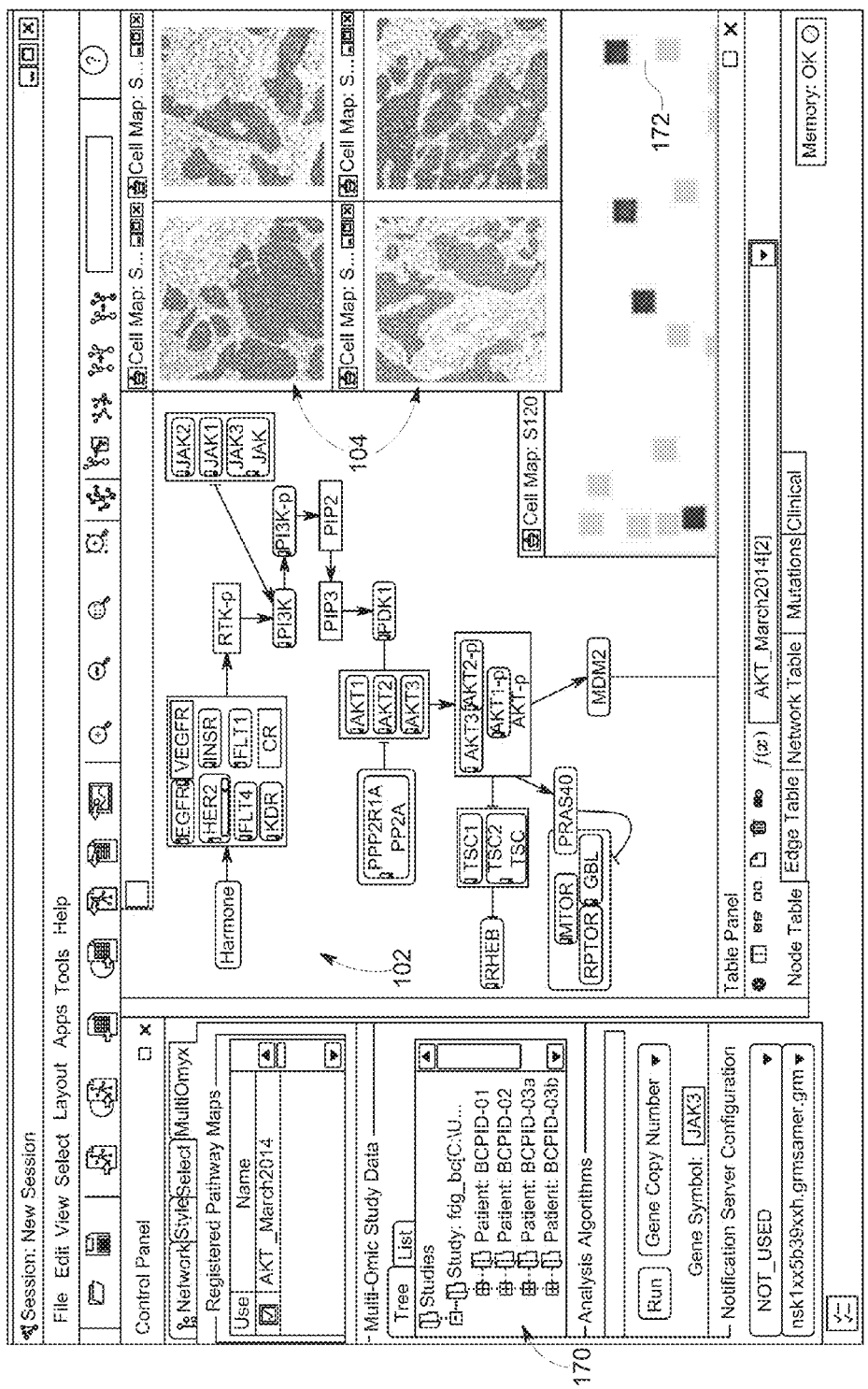

Further, turning to FIGS. 9A and 9B, an example is provided of a tool implementation that is configured to highlight cells in different fields of view taken from different spatial locations of the same tissue sample. For example, in sample screen 170 of FIG. 9A a slide view pane 172 is depicted showing the layout of a slide 90 having a tissue sample undergoing analysis, where different fields-of-view 94 spatially distributed throughout the tissue sample have been imaged. A blowup of the slide view 172 is shown in FIG. 9B. Based on the settings of one or more nodes in the pathway 102, certain of the fields-of-view 94 may have imaged cells corresponding to the current state of the pathway map 102 and these cells may be highlighted. As a result, certain of the fields of view 94 may be highlighted or have highlighted cells, and these fields-of-view 94 may be shown in screen 170 of FIG. 9A as cells maps 104. Examples, of such highlighted fields-of-view 94 are shown in enlarged form at the bottom of FIG. 9B. In addition, as shown in FIG. 9B, for fields-of-view 94 where numerous cells meeting the pathway conditions are present, it may be desirable to identify these fields-of-view 94 for acquiring a tissue sample (indicated by sequencing regions 96, such as a 2 mm diameter sample area) for nucleic acid sequencing or other cellular analysis operations.

As shown in FIG. 9B, and as discussed with respect to FIG. 3, a given sequencing region or sample 96 may not correspond precisely to the geometric shape, spatial location, and/or size of a corresponding field-of-view 94, though in other embodiments they may so correspond. Thus, it should be appreciated that, due to differences between the size, shape, or spatial location of a sequencing region 96 and a corresponding field-of-view 94, the sequence or other nucleic acid data for a given sequencing region 96 may be based on or encompass some number of cells outside the field-of-view 94 or for which interest is limited.

Further, sequencing or other nucleic acid information obtained for a given sequencing region 96 may be representative of the region 96 taken as a whole (i.e., may be averaged or aggregated for the corresponding region 96) and, thus, may not provide data at the cellular or sub-cellular level in the manner that biomarker type data may be available for a corresponding field-of-view 94. As will be appreciated, this distinction will depend on the sampling and sequencing methodologies employed, and to the extent that sequence data may be obtained at the cellular or sub-cellular level, this distinction may not apply. For example, to the extent that the sampling technique allows for selecting individual cells or a limited number of cells (e.g., 5, 10, 20, and so forth) within the field-of-view 94, the sequencing or other nucleic acid data derived for a given sampled region 96 may correspond closely to or precisely with cells of interest within the corresponding cell maps 104.

Figure 10:
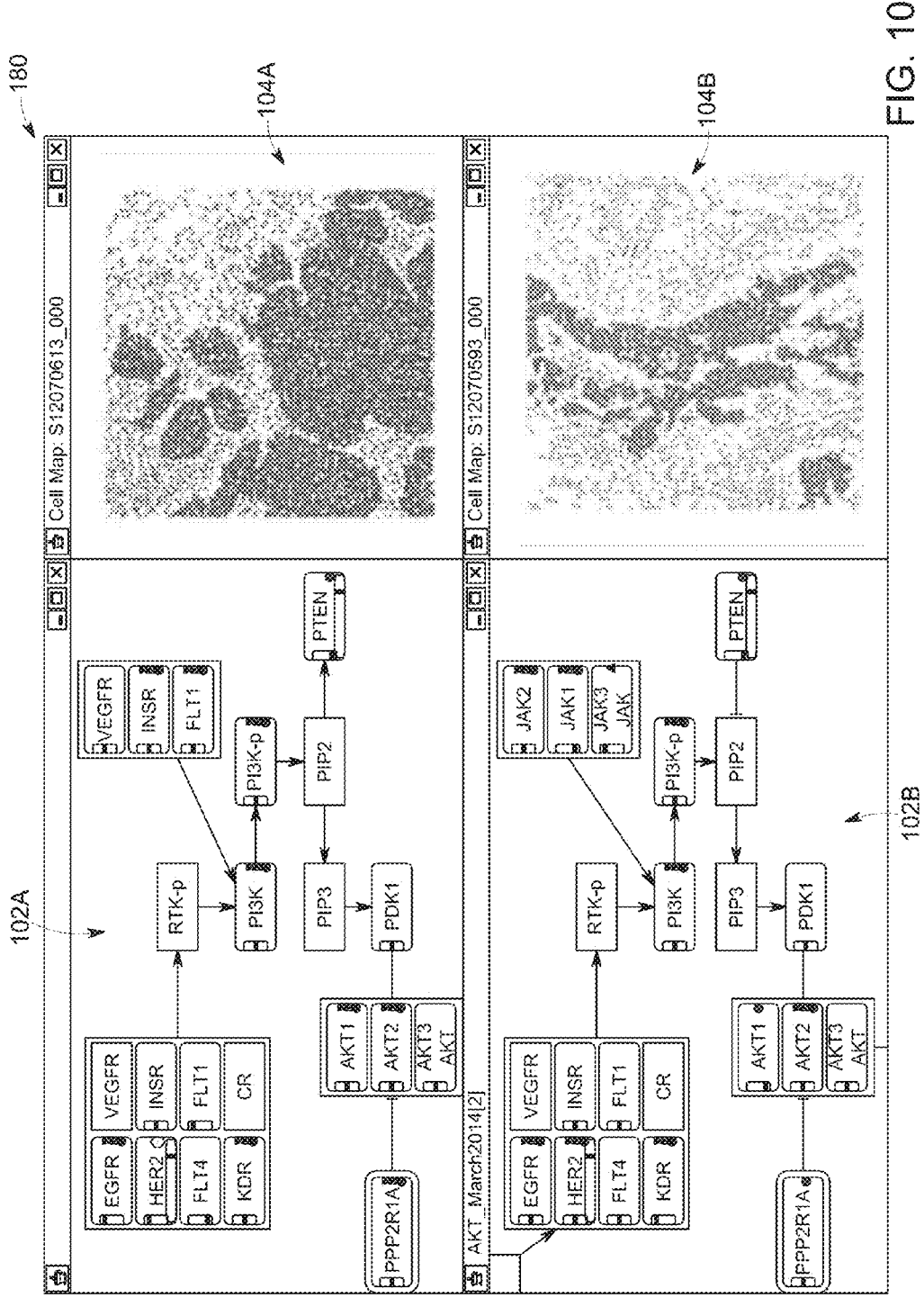
FIG. 10 shows a sample screen depicting associated cell image and pathway map data, in accordance with further aspects of the present disclosure.

Turning to FIG. 10, it should also be appreciated that the present approach and tools provide additional flexibility, such as being able to compare pathway map data for different patients. For example, in the example screen 180, an implementation is shown where a reviewer has loaded two copies (102A, 102B) of the same pathway map for comparison of different cells or tissues within a patient (i.e., a different copy of the pathway map 102 for each selected set of cells or tissues) or for comparison of different patients (i.e., a different copy of the pathway map 102 for each patient). In this manner, different cells or tissues, either from the same individual or different individual, can be compared in the pathway context. As will be appreciated, while the present example is of two copies of the pathway map 102, in practice more copies of the pathway map (and hence more comparisons) may be displayed and compared, within the limits imposed by available computation power and display space.

In such an implementation, a reviewer may select cells (e.g., cancer or tumor cells) within each cell map (e.g., 104A or 104B) and, based upon the measured or acquired biomarker expression and/or nucleic acid data, the respective linked pathway map (e.g., 102A or 102B) may be updated by setting nodes in the respective pathway map based on the measured cell data. The reviewer may then compare pathway maps to find distinctions between the selected cells and/or patients.

Figure 11:
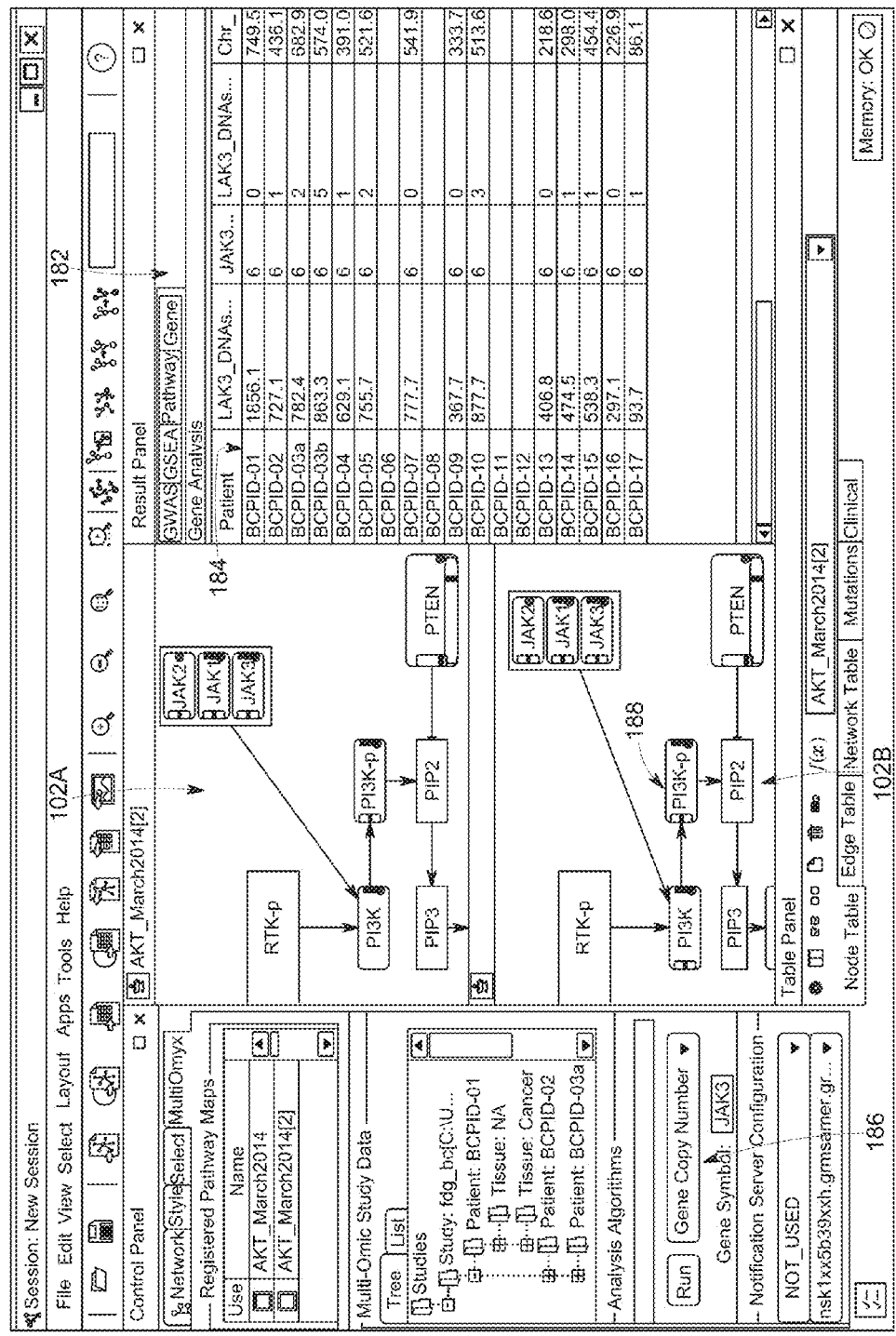
FIG. 11 shows a sample screen depicting annotated pathway map data and tabular analysis results, in accordance with aspects of the present disclosure.

Turning to FIG. 11, based on the comparison pathways, a reviewer may view the details of a node in question (e.g., the inferred JAK3 node 188) in a more detailed format, e.g., a table 182. In this example, for instance, the table 182 shows the results of a Gene Copy Number algorithm 186 and that the computed copy number for the JAK3 gene for the patient (i.e., patient 184) associated with pathway 102B was 2.5. From the table, a researcher can see that the p-value for the computed copy number is 0.008, which could be considered statistically significant.

Figure 12:
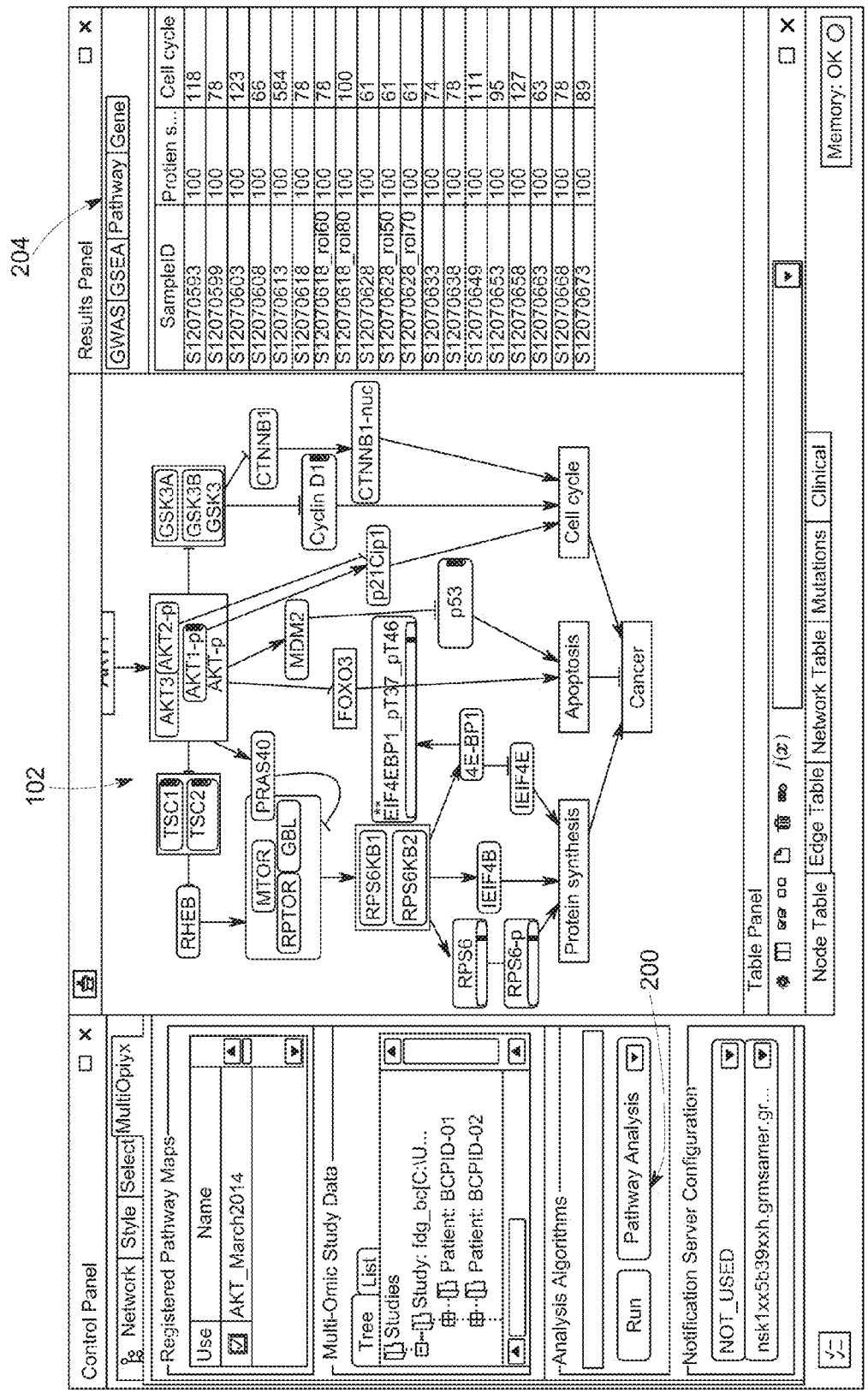
FIG. 12 shows a sample screen depicting pathway map data and tabular analysis results, in accordance with further aspects of the present disclosure.

In addition, based on a pathway map 102 that has been specified or set, such as by selection of a selected set of cells within a cell map 104, a scoring algorithm may be applied to generate a score for the pathway map 102. In such an implementation, the scoring algorithm (e.g., Pathway Analysis algorithm 200 of FIG. 12) that is run will score the selected pathway map 102 based on one or more criteria. For example, in one embodiment, scores may be computed for the map's end point nodes for one or more of protein synthesis, cell cycle, apoptosis, and/or cancer. Scores may be computed by such an algorithm using DNA sequence data or other available subject or tissue measures linked to the evaluated pathway map 102. Scores for each pathway endpoint node may be computed and displayed, such as in a table 204. As will be appreciated, such pathway map endpoint scores obtained for multiple patient pathway maps may be used to stratify or otherwise characterize patients.

Figure 13:
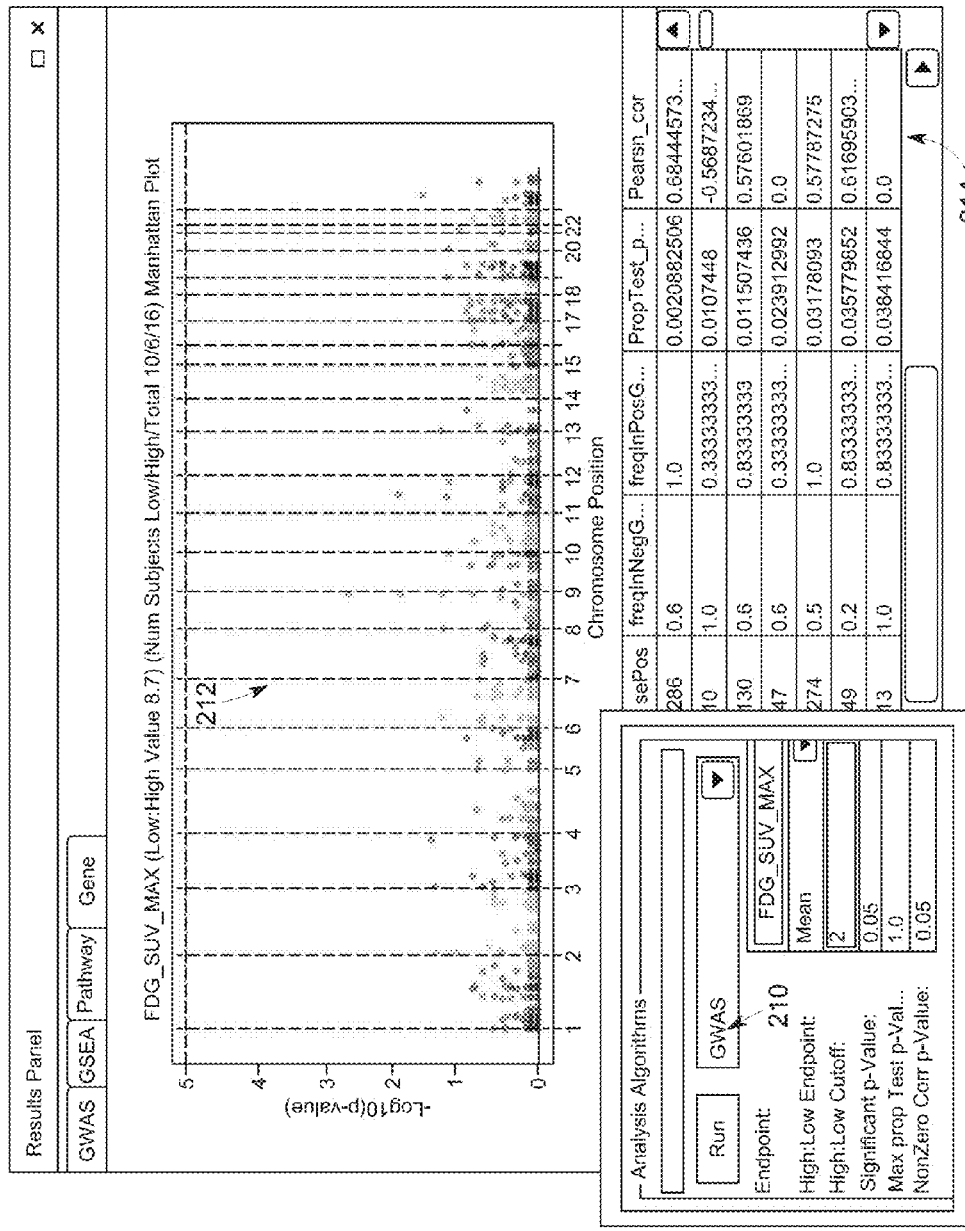
FIG. 13 depicts a statistical analysis for a GWAS analysis, in accordance with further aspects of the present disclosure.

As will be appreciated, other types of analyses may be implemented as part of such a tool. For example a Genome-Wide Association Study (GWAS) 210 may instead be selected and run as an analysis algorithm. Such an analysis will find associations of common genetic variants in different subjects with a specific phenotype or end point measure. The input to the GWAS algorithm consists of a list of samples and their phenotype values and a list of DNA variants present in one or more of the samples, as may be obtained by use of an analysis tool using the approaches discussed herein. The GWAS algorithm processes each variant, computing its frequency of being observed or not in the different phenotype groups. The algorithm then computes a Pearson's Chi Square test statistic for each variant to evaluate how probable the observed frequencies differ from the expected frequencies that would occur due to random chance. Results of one such analysis are shown in FIG. 13, which shows a Manhattan Plot 212 of the DNA sequencing variants by their chromosome position (x-axis) vs their association p-value to the endpoint measure of FDG uptake (y-axis). The red dotted line near the top of the plot is the y-value required for a data point to be considered statistically significant after accounting for multiple testing. The table 214 shows the variants associated with the FDG_SUV_MAX endpoint measure across all subject samples. The table list was sorted by each variant's association p-value of significance.

Similarly, a gene set enrichment analysis (GSEA) may be one of the analysis algorithms employed or provided in accordance with the present approach. Such an analysis may accept as inputs a list of gene measurements made on multiple samples with each sample assigned to a specific phenotype. The gene measures could be RNA or protein expression measures, or the presence of DNA variants in the genes. The GSEA algorithm may also be provided one or more gene sets that can come from a gene set database, which may provide pathways and/or gene ontology sets. The algorithm then outputs the gene sets sorted by a p-value of their statistical significance. By way of example, in an embodiment, the implemented algorithm may compute a correlation to phenotype for each gene measure in the list, sort the gene list by computed correlation coefficients, compute enrichment scores for each gene set, and estimate a statistical significance level of each enrichment score adjusting for multiple testing.

By way of further example, a specific GSEA analysis using aspects of the above-described approach is provided. In this example, a GSEA algorithm incorporated as part of an analysis tool provides a data driven method for selecting a limited set of molecules of interest, or probes for such molecules, for a multi-molecular multiplexing study in which the expression and/or state of the molecules of interest are statistically correlated with the endpoint measure under study. The application of multiplexing IF study involves the step of selecting a list of probes (e.g., antibody markers) to use when staining the tissue samples for specific proteins (including proteins in a particular phosphorylation, binding, or activation state) or other molecules of interest (e.g., a nucleic acid strand having a specified sequence, and so forth. This process is straightforward if the specific molecules (e.g., proteins, RNA, and so forth) are already known, as is typically found in the clinical diagnosis setting. However, if instead the multiplexing study is being conducted in the discovery research setting, it may instead be of interest to use an unbiased, data driven method of selecting target molecules and their corresponding antibody probes. This may be particularly true if the investigator has existing data on the subjects such as DNA sequencing and/or RNA expression measures in addition to the clinical endpoint measurements under study.

The problem in such a context is to pick a limited set of molecules of interest that give the greatest amount of scientific information at the minimal amount of cost. For example, antibody probes used to visualize such molecules have a cost associated with them and tissue samples tend to be limited and are expensive to gather or purchase. The application of a GSEA provides a method of prioritizing molecules of interest (e.g. a given protein, a given protein state, an intermediary amino acid structure, and/or nucleic acid sequence) by their probability of being relevant and associated with the endpoint measure under study, thus providing the means to select a limited set of probes that will provide the most scientific benefit while minimizing the study's cost.

Figure 14:
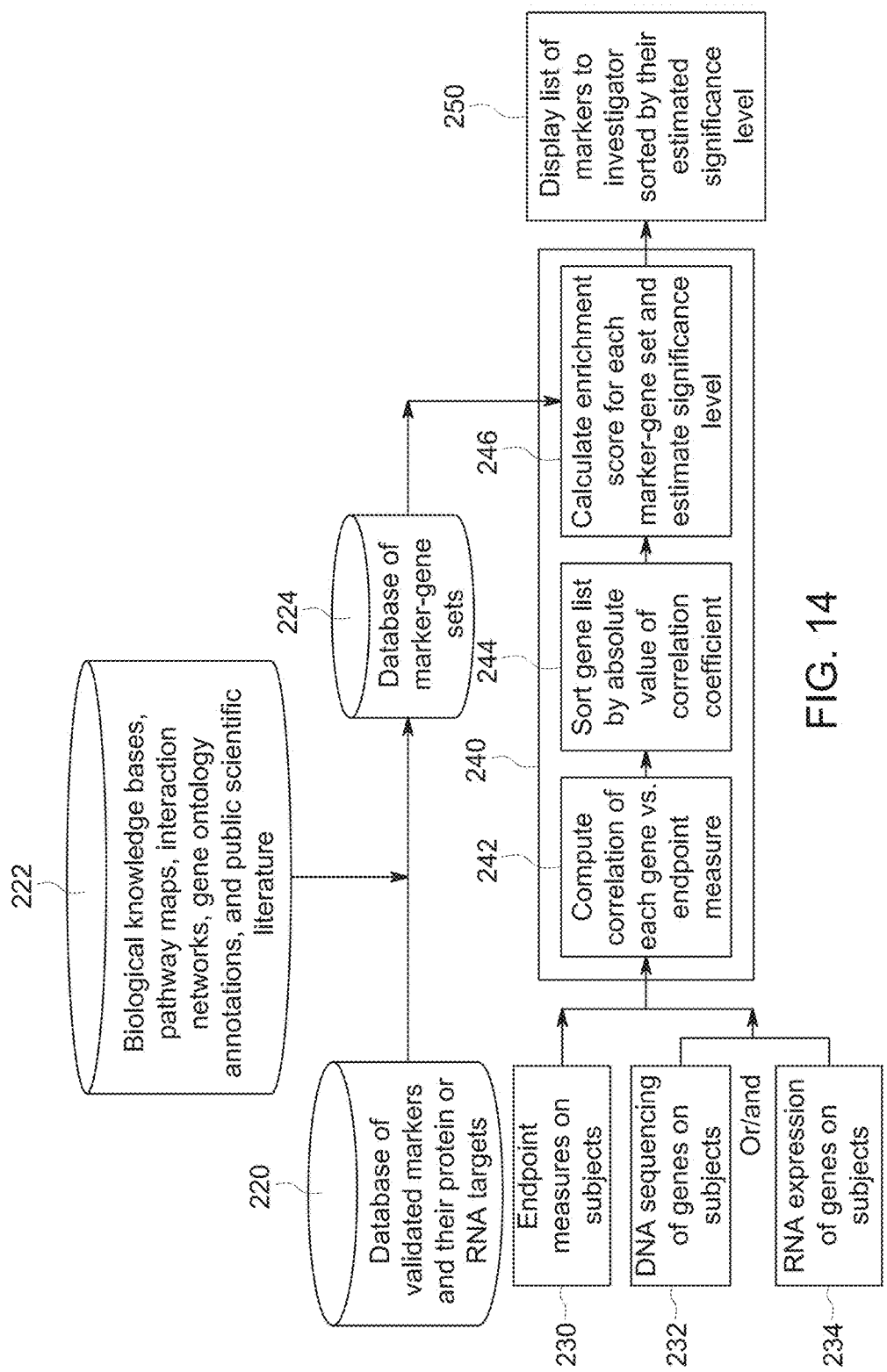
FIG. 14 depicts a process flow diagram for a GSEA analysis, in accordance with further aspects of the present disclosure.

Turning to FIG. 14, a data driven method to select molecules of interest and/or corresponding probes is illustrated, with examples components and steps to select a limited set of molecules of interest for a multiplexing study being shown. In this example, an existing database 220 of markers (e.g., probes) that have been validated for use in the multiplexing platform is accessed as an input. The other form of input 222 comes from existing biological knowledge bases of pathway maps, protein interaction networks, and gene ontology annotations, and public scientific literature. The marker database 220 and biological knowledge bases 222 are used to create a Marker-Gene Sets database 224. The Marker-Gene Sets database 224 contains for each validated marker a set of genes that are biologically associated with the gene targeted by the marker. The Marker-Gene Sets database 224 can be created in advance of any planned multiplexing studies and can be periodically updated as new validated markers become available and to reflect changes in the biological knowledge bases.

When an investigator is interested in conducting a multiplex study they often have a number of subjects in which they have endpoint measures 230. The endpoint measure 230 may come from imaging such as Positron emission tomography (PET), Computed Tomography (CT), or Magnetic resonance imaging (MRI), from patient outcome to a given therapy (e.g. recurrence status, survival), or some other clinical measurement or subject phenotype. For each subject, the investigator may have DNA sequencing data 232 and/or RNA gene expression (e.g., RNA microarray) measures 234 for one or more sequencing regions 96. This data in combination with the endpoint measures 230 (e.g., a selected endpoint phenotype) for each subject are used to perform an analysis 240 (such as a Gene Set Enrichment Analysis (GSEA), by way of example) represented by steps 242, 244, 246. This algorithm 240 can be used to compute the correlation of each gene measured by DNA sequencing or RNA gene expression with the endpoint measure under study (block 242). The list of all genes measured is then sorted by the absolute value of their correlation coefficient (block 244). The final step of the GSEA algorithm is to calculate (block 246) an enrichment score for each gene set and estimate its statistical significance level. The Marker-Gene Sets database 224 is used as the gene sets to work with by the GSEA algorithm at step 246. The list of Marker-Gene Sets is then sorted by their estimated significance level and is displayed (block 250) to the investigator. In one embodiment, the markers that are presented at the top of the list are those that are both validated and approved for use and also are likely to be associated with the endpoint measure under study.

While certain examples of analysis algorithms are noted in detail above, it should be appreciated that a variety of analysis algorithms and algorithm options that leverage both the pathway and cell image maps may be provided. Certain examples of such algorithms and options include, but are not limited to: options to highlight (or otherwise visually mark) pathway nodes 120 if they are a target for a validated antibody or are otherwise a measureable node; options to plot DNA sequencing mutations for a selected sample region 96 to a current pathway map 102; options to plot DNA FISH measures for selected cells in a current cell map 104 to a current pathway map 102; options to plot RNA expression measures for the selected sample region 96 to a current pathway map 102; options to plot IF protein measures for the selected cells in a current cell map 104 to a current pathway map 102; options to plot all available measures for the selected cells in a current cell map 104 to a current pathway map 102; options to visually highlight cells in a current cell map 104 using a current pathway map state; options to select cells in a current cell map 104 based on cell type; options to select cells in a current cell map 104 bounded by one or more defined regions-of-interest; options to select cells in a current cell map 104 bounded by one or more DNA sequencing regions-of-interest; options to select cells based on a biomarker(s) IF measurement(s); options to find the shortest path (e.g., edge connection) between two selected nodes 120 in a pathway map 102; options to display the gene copy number for a user-inputted gene symbol; and options to create threshold for a study and/or for each slide within a study using available field-of-view single cell analysis (SCA) data (e.g., thresholds may be created for one or more of 2, 3, 4, or 5 state models). Where appropriate, for one or more of the presented options a user may specify threshold values (e.g., low, medium, high, average, median, mode, and so forth based on a given statistical distribution or approach) to be met for implementations of the respective option.

With the preceding discussion and examples in mind, it should be appreciated that the present approaches and related tools may be useful in a generalized sense for aggregating and analyzing molecular data and biochemical or regulatory pathways in a variety of different contexts. For example, using one or more of the features and operations described above, users may be able to perform an analysis or study that leverages both sequence and image data to generate hybrid images that may be useful in clinical, diagnostic or research contexts.

Figure 15:
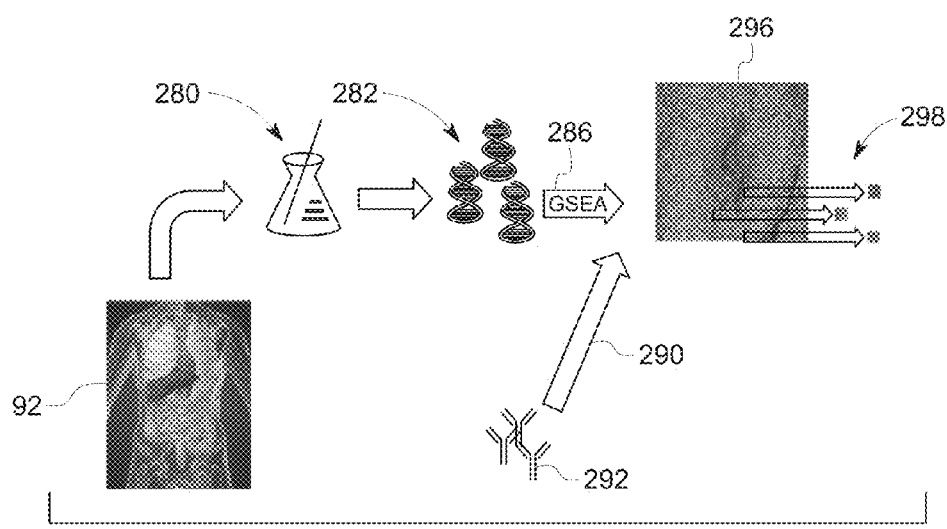
FIG. 15 depicts a process flow illustrating identification of regions of interest using the present approaches, in accordance with further aspects of the present disclosure.

By way of example, and turning to FIG. 15, a high-level view of one potential study protocol is shown that may employ certain of the techniques discussed herein. In this example, a tissue sample 92 is acquired from a subject and some subset of cells (e.g., a tumor, lesion, or other abnormality) of the sample 92 are sequenced 280 to derive nucleic acid sequence information 282 (e.g., mutation sequence data) for the cells in question. In one embodiment, the sequencing 280 is performed on cells in a heterogeneous or other non-specific context so that the sequence information 282 is not tied to a spatial context present in images of the tissue sample 92. Conversely, in other embodiments the sequencing 280 is performed on a generally homogeneous sample of cells derived from a localized region (e.g., a tumor, lesion, or other abnormality) within the tissue sample 92. Based on the sequence date 282, a GSEA analysis 286 (as described herein) or other sequence analysis may be conducted and a suitable set of IF probes 290 (e.g., labeled or tagged antibodies) selected from a larger catalog of available probes 292. The tissue sample 92 (e.g., slides formed from the tissue sample) may then undergo multiplexed IF imaging using the selected antibodies 290 to generate multiplexed IF images 296 which depict the spatial locations of the selected mutations within the tissue sample 92. Based on these images, a user may then identify, extract, view, and/or analyze regions of interest 298 (e.g., specific fields of view) within the multiplexed IF tissue sample images 296. Thus, in this example, sequence or mutation information 282 for a tissue sample 92 may be used to select markers (e.g., probes) 290, which may then be used in a multiplexed imaging approach to visualize cells of interest within a sample based on the initial sequence analysis. It should also be appreciated that certain of these steps and actions may be iteratively performed. By way of example, once one or more regions of interest 298 are identified in the multiplexed tissue sample image 296, cell samples may be extracted from these regions-of-interest within the tissue sample for further sequencing and analysis, which may lead to the selection of additional probes for use in additional imaging rounds.

Figure 16:
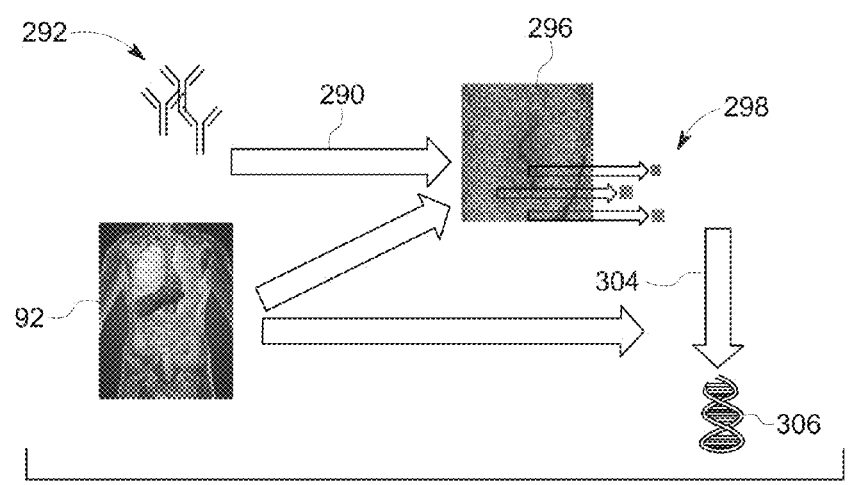
FIG. 16 depicts a process flow illustrating acquisition of DNA sequence data in a homogeneous context using the present approaches, in accordance with further aspects of the present disclosure.

Conversely, the tools and techniques discussed herein may be used to facilitate other analyses or data acquisitions, such as to acquire a mutational profile for spatially-selected regions. For example, turning to FIG. 16 a further high-level view is depicted of a different study protocol employing techniques and tools discussed herein to acquire spatially-selected DNA sequence data. In this example, a tissue sample 92 undergoes multiplexed IF imaging using probes 290 selected from a library of probes 292 and corresponding to molecules determined to be of interest, resulting in one or more multiplexed IF images 296 immunofluorescently tagged for biomarker expression deemed of interest. From within the multiplexed IF images 296, regions-of-interest 298 may be identified or extracted that spatially localize expression activity of interest (e.g., protein, nucleic acid, or other biological expression) within the tissue sample 92. Cells samples may then be taken (e.g., at one or more sampling or sequencing regions 96) that correspond to the identified spatial locations within the tissue sample 92 and sequencing 304 may be performed on the spatially selected cells to generate a mutational profile 306 that is generally specific to the cells within the identified spatial regions-of-interest 298. It should also be appreciated that certain of these steps and actions may be iteratively performed. By way of example, once sequence data has been obtained for cells in the one or more regions of interest 298, additional probes may be identified for newly identified molecules of interest, and the tissue sample 92 reimaged using the newly selected probes. In this manner, additional regions of interest can be identified and subsequently sequenced. Such an approach may be of particular interest in fields such as oncology where identification of localized mutations and aberrant expression events is of particular interest.

Technical effects of the invention include the dynamic linking of displayed pathway maps and cell maps, where the pathway maps are linked to spatially-localized regional nucleic acid data (e.g., sequence data), as opposed to non-spatially selected nucleic acid data. The pathway map and cell map data is linked so that interactions (e.g., selections of cells, setting of node values or states, and so forth) results in changes or updates to the linked map, such as the selection or highlighting of cells exhibiting pathway map characteristics specified by a user or updating node values or states to correspond to that of a cell or cells selected by the user.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-based method for interactively evaluating image and data for a tissue sample, comprising:
   displaying a pathway map comprising a plurality of nodes linked to nucleic acid sequence data for one or more spatially localized regions-of-interest within a tissue sample;
   displaying a cell map depicting a set of cells present within a field-of-view of the tissue sample, wherein the cell map is linked to a plurality of biomarker expression data displayed for the tissue sample;
   receiving one or more inputs specifying values or states for one or more nodes of the pathway map; and
   based on the one or more inputs, highlighting cells within the cell map that exhibit biomarker expression corresponding to the values or states specified for the one or more nodes.

2. The computer-based method of claim 1, wherein the regions-of-interest for which nucleic acid sequence data is known differ in one or both of size or shape from the fields-of-view associated with the cell map.

3. The computer-based method of claim 1, wherein the nucleic acid sequence data is averaged or aggregated for a respective region-of interest.

4. The computer-based method of claim 1, wherein the biomarker expression data is at the cellular or sub-cellular level for cells within the cell map.

5. The computer-based method of claim 1, wherein the biomarker expression corresponds to a mutation profile characterized by the values specified for the one or more nodes by the inputs.

6. The computer-based method of claim 1, wherein the pathway map and the cell map are displayed concurrently and wherein receipt of the one or more inputs, or changes to the inputs, dynamically updates the highlighting of cells.

7. The computer-based method of claim 1, wherein the pathway map comprises a metabolic pathway map or signaling pathway map.

8. The computer-based method of claim 1, wherein the one or more inputs specifying values or states for one or more nodes of the pathway map comprises user selections of a cell or subset of cells in the cell map.

9. The computer-based method of claim 1, wherein one or more of the nodes are displayed with visual indicators conveying information about biomarker expression or nucleic acid sequence for the respective node.

10. The computer-based method of claim 9, wherein the conveyed information comprises one or more of biomarker expression, inferred gene copy number, DNA sequencing variant impact, RNA expression, or immunofluorescence protein measures.

11. The computer-based method of claim 1, wherein the one or more inputs specify a value or state related to a gene copy number, DNA sequence variant impact, RNA expression measure, or immunofluorescence protein expression measure.

12. A computer-based method for interactively evaluating image and data for a tissue sample, comprising:
   displaying a pathway map comprising a plurality of nodes linked to nucleic acid sequence data for one or more spatially localized regions-of-interest within a tissue sample;
   displaying a cell map depicting a set of cells present within a field-of-view of the tissue sample, wherein cell map is linked to a plurality of biomarker expression data for the tissue sample;
   receiving one or more inputs selecting one or more cells of the cell map; and
   based on the one or more inputs, setting values or states of one or more nodes within the pathway map to correspond to the nucleic acid characteristics of the one or more selected cells.

13. The computer-based method of claim 12, wherein the nucleic acid sequence data is averaged or aggregated for a respective region-of interest.

14. The computer-based method of claim 12, wherein the biomarker expression data is at the cellular or sub-cellular level for cells within the cell map.

15. The computer-based method of claim 12, wherein the nucleic acid characteristics of the one or more selected cells correspond to a mutation profile for the one or more selected cells.

16. The computer-based method of claim 12, wherein the pathway map and the cell map are displayed concurrently and wherein receipt of the one or more inputs, or changes to the inputs, dynamically updates the highlighting of cells.

17. The computer-based method of claim 12, wherein the one or more inputs selecting one or more cells of the cell map select cells exhibiting biomarker expression for one or more biomarkers associated with a mutation profile.

18. A processor-based system, comprising:
   one or both of a memory or storage device storing one or more executable routines for the analysis of region-specific nucleic acid sequence data and cellular or sub-cellular biomarker expression data;
   one or more processors configured to execute the one or more executable routines which, when executed, cause acts to be performed comprising:
   displaying a pathway map comprising a plurality of nodes linked to nucleic acid sequence data for one or more spatially localized regions-of-interest within a tissue sample;
   displaying a cell map depicting a set of cells present within a field-of-view of the tissue sample, wherein the cell map is linked to a plurality of biomarker expression data for the tissue sample;
   receiving inputs setting one or more node values or states within the pathway map or selecting one or more cells within the cell map; and
      if the inputs set one or more node values or states within the pathway map, highlighting cells within the cell map that exhibit biomarker expression corresponding to the values or states specified for the one or more nodes;
      or if the inputs select one or more cells within the cell map, setting values of one or more nodes within the pathway map to correspond to the nucleic acid characteristics of the one or more selected cells.

19. The processor-based system of claim 18, wherein the regions-of-interest for which nucleic acid sequence data is known differ in one or both of size or shape from the fields-of-view associated with the cell map.

20. The processor-based system of claim 18, wherein the nucleic acid sequence data is averaged or aggregated for a respective region-of interest.

21. The processor-based system of claim 18, wherein the biomarker expression data is at the cellular or sub-cellular level for cells within the cell map.

22. The processor-based system of claim 18, wherein the pathway map and the cell map are displayed concurrently and wherein receipt of the one or more inputs, or changes to the inputs, dynamically updates the highlighting of cells.

* * * * *